United States Patent [19]

Schmidt et al.

[11] Patent Number: 4,605,666

[45] Date of Patent: Aug. 12, 1986

[54] PROCESS FOR PREPARING SPRAY-DRIED POWDERS CONTAINING A WATER-SOLUBLE VITAMIN AND POWDERS PREPARED THEREBY

[75] Inventors: Douglass N. Schmidt, Grosse Ile; Jeffrey L. Finnan, Southgate; Rudolph E. Lisa, Grosse Ile, all of Mich.

[73] Assignee: BASF Corporation, Wyandotte, Mich.

[21] Appl. No.: 686,143

[22] Filed: Oct. 23, 1984

Related U.S. Application Data

[63] Continuation-in-part of Ser. No. 544,522, Oct. 24, 1983, abandoned.

[51] Int. Cl.$^4$ ............................................. A61K 31/365
[52] U.S. Cl. ..................................... 514/474; 514/960
[58] Field of Search ................................ 514/474, 960

[56] References Cited

U.S. PATENT DOCUMENTS

| | | | |
|---|---|---|---|
| 3,266,992 | 8/1966 | de Jong | 424/280 |
| 3,293,132 | 12/1966 | Stoyle et al. | 424/280 |
| 3,396,226 | 8/1968 | Cavalli et al. | 424/280 |
| 3,852,421 | 12/1974 | Koyanagi et al. | 424/280 |
| 4,036,948 | 7/1977 | Kitamori et al. | 424/280 |
| 4,352,821 | 10/1982 | Doran et al. | 424/361 |
| 4,389,393 | 6/1983 | Schor et al. | 424/19 |
| 4,533,674 | 8/1985 | Schmidt et al. | 514/474 |

OTHER PUBLICATIONS

Chem. Abst. 99, 218464(v), (1983)–Velilcova et al.

Primary Examiner—Douglas W. Robinson
Attorney, Agent, or Firm—David L. Hedden; Joseph D. Michaels

[57] ABSTRACT

The subject invention relates to a process for preparing a powder containing a water-soluble vitamin which is directly compressible into a tablet prepared by spray drying (a) an aqueous slurry of a water-soluble vitamin and a binder; (b) preferably an adsorbent; and (c) a lubricant. Particularly useful water-soluble vitamins are ascorbic acid, sodium ascorbate, and calcium ascorbate. The unique feature of the process is that the lubricant is spray dried along with the other components.

The invention also relates to powders prepared by this process. The powders are directly compressible into tablets and will not demix.

11 Claims, No Drawings

PROCESS FOR PREPARING SPRAY-DRIED POWDERS CONTAINING A WATER-SOLUBLE VITAMIN AND POWDERS PREPARED THEREBY

CROSS REFERENCE TO RELATED APPLICATIONS

This application is a continuation-in-part of U.S. application Ser. No. 544,522 filed on Oct. 24, 1983, now abandoned.

BACKGROUND OF THE INVENTION

1. Field of the Invention

This invention relates to spray-dried water-soluble vitamin powders which are directly compressible into tablets, and the powders prepared thereby. Particularly useful water-soluble vitamins are ascorbic acid, sodium ascorbate, and calcium ascorbate.

2. Description of the Prior Art

U.S. Pat. No. 3,293,132 describes a continuous process for making a vitamin C powder by spray drying. The process involves spray drying from 75 to 95 parts by weight of ascorbic acid, from 5 to 25 parts by weight of a carbohydrate, and from 0.5 to 5 parts by weight of a film-producing hydrophilic, organic colloid material such as gelatin, water-soluble derivatives of casein, water-soluble gums, and water-soluble derivatives of cellulose. Although the process is continuous, a lubricant is not one of the spray dried components. Instead, the lubricant is blended into the spray-dried powder after spray drying. Consequently, the powder taken directly from the spray dryer cannot be directly compressed into tablets. Moreover, the powder disclosed in this patent is likely to discolor at use conditions.

SUMMARY OF THE INVENTION

The subject invention relates to free flowing powders containing a water-soluble vitamin powder prepared by spray drying an effective amount of (a) an aqueous slurry of a water-soluble vitamin and a binder; (b) preferably an adsorbent; and (c) a lubricant. The process is unique because the lubricant is mixed with all of the other components during the spray-drying.

The invention also relates to the powders prepared by this process. The powders are directly compressible into tablets without needing the addition of other excipients, and are unique because they do not demix. They are also color stable tablets which have acceptable disintegration times and hardness.

DESCRIPTION OF THE PREFERRED EMBODIMENT

The powders of this invention which contain a water-soluble vitamin are prepared by spray drying an aqueous slurry of a water-soluble vitamin and a binder in the presence of a lubricant and preferably an adsorbent. In general, any water-soluble vitamin can be used in the process. Specific examples include ascorbic acid, sodium ascorbate, calcium ascorbate, niacin, riboflavin, pyridoxine, calcium d-pantothenate, thiamine hydrochloride, thiamine nitrate, pantothenic acid, folic acid, and biotin. Of more interest, however, are ascorbic acid, sodium ascorbate, and calcium ascorbate. Natural sources of these water-soluble vitamins, such as rosehips, may also be used, preferably in minor amounts.

Typical binders (for example, see U.S. Pat. No. 3,293,132 at column 3, lines 29-54) that can be used include proteins such as gelatin, water-soluble derivatives of casein, e.g., sodium caseinate, and the like; water-soluble gums such as gum acacia, gum karaya, gum ghatti, tragacanth, and the like; cellulose, and water-soluble derivatives of cellulose such as methylcellulose, hydroxyethyl cellulose, sodium carboxymethylcellulose, and the like. For this purpose, use may furthermore be made of certain polyvinyl resins such as, for example, polyvinyl alcohol, polyvinyl pyrrolidine and the like. Preferably used with ascorbic acid, sodium ascorbate, and calcium ascorbate are microcrystalline cellulose, and mixtures of microcrystalline cellulose and hydroxypropylmethylcellulose.

To prepare the aqueous slurry, the water-soluble vitamin and binder are added to enough water to make a finished feed slurry having about 10 to 90 percent solids by weight, and, preferably, about 50 to 75 percent by weight solids.

The aqueous slurry containing the water-soluble vitamin and binder is preferably spray dried in the presence of an adsorbent such as those disclosed in U.S. Pat. No. 3,914,430 at column 3, lines 43-68, which is hereby incorporated by reference. Preferably used as the adsorbent is silicon dioxide, particularly silicon dioxide having a particle size of from 0.1 to 10.0 microns.

As was indicated previously, a lubricant is an essential component of the powder and may be incorporated into the powder product by spray drying the aqueous slurry of water-soluble vitamin and microcrystalline cellulose in the presence of the lubricant in addition to the adsorbent. However, the preblending step to mix the absorbent and lubricant can be eliminated by adding the lubricant to the slurry and spray drying the slurry plus lubricant in the presence of only the adsorbent. Preferably used as the lubricant are stearic acid, magnesium stearate and mixtures thereof. However, other stearic acids salts may be used such as calcium stearate. Also, there can be used wax-like materials, for instance, wax-like saturated fatty acids, wax-like mixtures containing two or more saturated fatty acids or wax-like hydrogenated glyceride, in admixture with a metallic stearate and/or titanium dioxide such as are disclosed in U.S. Pat. No. 3,396,226 (column 3, lines 29-55) which is hereby incorporated by reference.

Additional excipients may also be used in preparing the subject powders. Although not used on a preferred basis because of nutritional factors, the subject powders may also contain carboxyhydrates such as sugars including lactose, sucrose, maltose, glucose, mannose, fructose, arabinose, and the like; non-sugars such as pectin, starch, and the like; and closely related polyhydric alcohols containing from 4 to 6 hydroxyl radicals such as mannitol, dulcitol, sorbitol, and the like.

The components described herein are used in effective amounts. Those skilled in the art can determine what amounts are to be used based upon their own experience and the examples set forth herein. However, when ascorbic acid, sodium ascorbate, and calcium ascorbate are used as the water-soluble vitamin, the components described herein are added in amounts such that the final powder formed will contain at least 80 (preferably at least 90) percent by weight of the water-soluble vitamin, less than 15 (preferably less than 9) percent by weight of binder, 0.2 to 2 percent by weight of adsorbent, and 0.2 to 5 percent by weight of the lubricant and less than 3 percent of other excipients. Although these amounts may also be effective for other water-soluble vitamins, those skilled in the art may discover better proportions with them and for specific purposes.

Any suitable spray drier may be used to prepare the powders of this invention such as vertical spray drier equipped with a means of making droplets, such as a rotary atomizer operated between 10,000 and 35,000 rpm, preferably 18,000 to 25,000 rpm for a small dryer or suitable atomizer nozzles (such as high pressure, two- and three-fluid). The inlet temperature is maintained at 190° C. to 200° C. and the outlet temperature is a function of the inlet temperature and flow rate, generally between 90° C. to 100° C. From 0.5 to 2.5 percent by weight, based on the weight of the dry powder of silicon dioxide and from 0.5 to 5.0 percent of the lubricant is added to the spray drier chamber, preferably at a point of negative pressure. The aqueous slurry of water-soluble vitamin and microcrystalline cellulose is then spray dried to form a free-flowing, nonagglomerated powder.

Tablets from the powder are made by conventional methods. Useful tabletting aids are disclosed in *Pharmaceutical Technology*, July, 1980, pages 27–35, and 62.

The examples which follow will provide more details regarding how to practice the invention. In the examples, unless otherwise stated, all parts are by weight and all temperatures are in degrees centigrade.

EXAMPLE 1

An aqueous slurry containing 60 percent by weight solids was formed by adding 9286 parts of ascorbic acid and 714 parts of microcrystalline cellulose to water held in a stainless steel jacketed tank equipped with a turbine agitator. The aqueous slurry was sprayed into a four foot diameter vertical spray drier through a rotary atomizer at 20,000 to 23,000 revolutions per minute. About 1.0 percent by weight of silicon dioxide (sold under the trade name AEROSIL 200), and 1.0 percent by weight of magnesium stearate were added into the drying chamber at a point of negative pressure.

The resulting spray-dried powder contained:

| Component | Percent by Weight Based on the Weight of the Dry Powder |
|---|---|
| Ascorbic acid | 90.0 |
| Microcrystalline cellulose | 7.0 |
| Silicon dioxide | 1.0 |
| Magnesium stearate | 1.0 |
| Moisture | 1.0 |

The particle size of the powder was such that 15 to 40 percent of the powder was retained on a 200 mesh screen, 40 to 65 percent of the powder was retained on a 325 mesh screen, and 5 to 30 percent of the powder was able to pass through a 325 mesh screen.

Tablets were made on a single rotary tablet press at 30 revolutions per minute. The resulting tablets had a hardness of 14.0 (SCU), a friability percent of 3.90 which was measured as loss after 120 revolutions in a Vandercamp friabilator, and a disintegrating time of 3.9 minutes in water at 37° C. in a Vandercamp disintegration/dissolution tester.

EXAMPLE 2

A suspension was made in a stainless steel jacketed tank equipped with an agitator by adding water to 102 parts of hydroxypropylmethylcellulose such that the resulting suspension had a solids weight of 7.5 percent by weight. The suspension was heated to about 80° C. and then cold water was added in an amount such that the suspension had 2.25 percent solids. Then 5572 parts of ascorbic acid and 274 parts of microcrystalline cellulose were added.

The resulting slurry was sprayed into a nine foot diameter vertical spray drier through a rotary atomizer at 10,000 to 14,000 revolutions per minute. About 1.0 percent by weight of silicon dioxide (sold under the trade name AEROSIL 200) and 2.0 percent by weight of stearic acid were added into the drying chamber at a point of negative pressure.

The resulting yield was 5882 parts of a spray dried powder which contained:

| Component | Percent by Weight Based on the Weight of the Dry Powder |
|---|---|
| Ascorbic Acid | 90.5 |
| Microcrystalline cellulose | 4.6 |
| Hydroxypropylmethylcellulose | 1.4 |
| Silicon dioxide | 1.0 |
| Stearic acid | 2.0 |
| Moisture | 0.5 |

The resulting tablets had a hardness of 15.0 (SCU), a friability of 2.14 percent, and a disintegration time of 21 minutes.

EXAMPLE 3

A suspension was made in a stainless steel jacketed tank equipped with an agitator by adding water to 200 parts of hydroxypropylmethylcelluose such that the resulting suspension had a solids weight of 6.7 percent by weight. The suspension was heated to about 80° C., and then cold water was added in an amount such that the suspension had 2.32 percent solids. Then 433 parts of microcrystalline cellulose and 200 parts of stearic acid were added.

The resulting slurry was sprayed through a two-fluid nozzle (2.9 mm diameter, 39 psig) from the bottom of a four-foot diameter spray drier into a counter current air stream. About 1.0 percent by weight of silicon dioxide was added into the drying chamber at a point of negative pressure.

The resulting powder contained:

| Component | Percent by Weight Based on the Weight of the Dry Powder |
|---|---|
| Ascorbic acid | 90.5 |
| Microcrystalline cellulose | 4.2 |
| Hydroxypropylmethylcellulose | 1.9 |
| Stearic acid | 1.9 |
| Silicon dioxide | 1.0 |
| Moisture | 0.5 |

The resulting tablets had hardness of 14.1 (SCU), a friability of 2.15 percent, and a disintegration time of 17 minutes.

EXAMPLE 4

A suspension was made in a stainless steel tank equipped with an agitator by adding hot water to 195 parts of hydroxypropylmethylcellulose such that the resulting suspension had a solids weight of 9.75 percent by weight. The suspension was heated on a hot plate to about 80° C. and then cold water was added in an amount such that the suspension had 3.17 percent solids.

Then 9290 parts of sodium ascorbate and 515 parts of microcrystalline cellulose were added, followed by 800 parts additional water.

The resulting slurry was sprayed into a four foot diameter vertical spray drier through a rotary atomizer at about 23,000 revolutions per minute. About 1.0 percent by weight of silicon dioxide (sold under the trade name Syloid 244FP) and 2.0 percent by weight of stearic acid were added into the drying chamber at a point of negative pressure.

The resulting yield was 10,600 parts of a spray dried powder which contained:

| Component | Percent by Weight Based on the Weight of the Dry Powder |
|---|---|
| Sodium Ascorbate | 87.6 |
| Microcrystalline cellulose | 4.9 |
| Hydroxypropylmethyl cellulose | 1.8 |
| Silicon dioxide | 1.0 |
| Stearic acid | 2.0 |
| Moisture | 3.0 |

The resulting tablets had a hardness of 13.6 (SCU), a friability of 0.44 percent, and a disintegration time of 28 minutes.

EXAMPLE 5

A suspension was made in a stainless steel tank equipped with an agitator by adding hot water to 195 parts of hydroxypropylmethylcellulose such that the resulting suspension had a solids weight of 7.9 percent by weight. The suspension was heated to about 80° C. on a hot plate and then cold water was added in an amount such that the suspension had 2.8 percent solids. Then 9290 parts of calcium ascorbate and 515 parts of microcrystalline cellulose were added, followed by an additional 600 parts water.

The resulting slurry was sprayed into a four foot diameter vertical spray drier through a rotary atomizer at 23,000 revolutions per minute. About 1.0 percent by weight of silicon dioxide (sold under the trade name Syloid 244FP) and 2.0 percent by weight of stearic acid were added into the drying chamber at a point of negative pressure.

The resulting yield was 10,532 parts of a spray dried powder which contained:

| Component | Percent by Weight Based on the Weight of the Dry Powder |
|---|---|
| Calcium ascorbate | 88.2 |
| Microcrystalline cellulose | 4.9 |
| Hydroxypropylmethyl cellulose | 1.9 |
| Silicon dioxide | 1.0 |
| Stearic acid | 2.0 |
| Moisture | 2.0 |

The resulting tablets had a hardness of 11.9 (SCU), a friability of 0.69 percent, and a disintegration time of >45 minutes.

These examples show that powders containing water-soluble vitamins can be prepared by spray drying the components, including the lubricant, by a continuous process to make a directly compressible powder that does not demix. The tablets formed with the powders have acceptable hardness, disintegration times, and color stability.

COMPARISON EXAMPLE

Following the procedure of Example 3, a spray-dried powder (Powder #1) was prepared having the following composition:

| Component | Percent by Weight Based upon the Dry Powder |
|---|---|
| Ascorbic Acid | 90.1 |
| Microcrystalline cellulose | 5.0 |
| Adsorbent (Hydrated Silica) | 1.0 |
| Hydroxymethyl cellulose | 1.9 |
| Lubricant (Stearic acid) | 2.0 |
| Moisture | 1.0 |
| | 100.0* |

Another powder (Powder #2) was prepared in the same way except the adsorbent and lubricant were not added to the spray drier, but were mixed in manually to the unlubricated, spray-dried powder so that the final composition of Powder #2 was essentially the same as Powder #1.*

*A small amount of lubricant (0.2%) and adsorbent (0.1%) were discharged into the spray drier during the spray drying process.

Powder #1 and Powder #2 were then tested to see whether they were susceptible to demixing. Powder #2 was first mixed for about 20 minutes in a blender without heating. Then two 11-inch tubes 1½ inches in diameter were filled with Powder #1 and Powder #2, and were sealed at both ends. These were then placed upright in a vibrating tray and vibrated for 4 hours. The cylinders were then divided into three equal portions—top, middle, and bottom. The top and bottom portions were then analyzed by gas chromatography using a capillary column, according to AR-14036, to determine the amount of stearic acid in each portion.

The percentage of stearic acid in the portions containing Powder #1 was 1.51 percent (top) and 1.57 percent (bottom). On the other hand the percentage of stearic acid in the portions containing Powder #2 was 1.52 percent (top) and 2.24 percent (bottom).

These results indicate Powder #2 experienced demixing because there is a difference of 0.72 percent between the amount of stearic acid in the two portions. This difference can lead to less uniformity in lubrication and can cause problems in tableting such as capping due to over lubrication, and die wall binding in the tablet press due to under lubrication. Note that the difference between the amount of stearic acid in the top and bottom portions of Powder #1, which was prepared in accordance with the subject matter, was only 0.06 percent.

The embodiments of the invention in which an exclusive property or privilege is claimed are defined as follows:

1. A process for preparing free flowing, lubricated, water-soluble vitamin powders, which are directly compressible into a tablet, which comprises spray drying
   an aqueous slurry of a water-soluble vitamin and a
      binder in the presence of a lubricant which is added
      to the drying chamber wherein the amounts of
      water-soluble vitamin, binder, and lubricant are
      such that the resulting powder will contain at least
      80 percent by weight of water-soluble vitamin, no
      more than 15 percent by weight of binder, and
      from 0.5 to 5.0 percent by weight of lubricant.

2. The process of claim 1 carried out in the presence of from 0.5 to 5.0 percent by weight of an adsorbent.

3. The process of claim 2 wherein the water-soluble vitamin is selected from the group consisting of ascorbic acid, sodium ascorbate, and calcium ascorbate.

4. The process of claim 1 wherein the lubricant is spray dried in admixture with the aqueous slurry of water-soluble vitamin and binder.

5. The process of claim 4 wherein the lubricant is selected from the group consisting of stearic acid, magnesium stearate, and mixtures thereof.

6. The process of claim 5 wherein the adsorbent is silicon dioxide.

7. The process of claim 6 wherein the silicon-dioxide has a particle size of about 0.1 micron to about 10.0 microns.

8. The process of claim 7 wherein the binder is microcrystalline cellulose.

9. The process of claim 8 wherein the powder contains at least 90 percent by weight of the water-soluble vitamin and no more than 9 percent by weight of microcrystalline cellulose.

10. The process of claim 9 which contains from 1.0 to 3.0 percent by weight of hydroxypropylmethylcellulose as an additional binder.

11. The process of claim 10 wherein the water-soluble vitamin is ascorbic acid.

* * * * *